United States Patent
Percival et al.

(10) Patent No.: US 10,493,101 B2
(45) Date of Patent: *Dec. 3, 2019

(54) ANTIMICROBIAL COMPOSITION

(71) Applicant: ConvaTec Technologies Inc., Las Vegas, NV (US)

(72) Inventors: Steven L. Percival, Chester (GB); Phillip G. Bowler, Warrington (GB); David Parsons, Wirral (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/372,299

(22) Filed: Dec. 7, 2016

(65) Prior Publication Data

US 2017/0079276 A1  Mar. 23, 2017

Related U.S. Application Data

(63) Continuation of application No. 14/795,176, filed on Jul. 9, 2015, now Pat. No. 9,545,390, which is a (Continued)

(30) Foreign Application Priority Data

Dec. 14, 2005 (GB) .................................. 0525504.7

(51) Int. Cl.
  *A61K 33/38* (2006.01)
  *A61K 31/198* (2006.01)
  (Continued)

(52) U.S. Cl.
  CPC .............. *A61K 33/38* (2013.01); *A01N 37/44* (2013.01); *A01N 59/00* (2013.01); *A01N 59/12* (2013.01);
  (Continued)

(58) Field of Classification Search
  None
  See application file for complete search history.

(56) References Cited

U.S. PATENT DOCUMENTS 2,396,514 A  3/1946  Kreidl et al.
2,785,106 A  3/1957  Mendelsohn
(Continued)

FOREIGN PATENT DOCUMENTS

CN  101076251 A  11/2007
CN  101331263 A  12/2008
(Continued)

OTHER PUBLICATIONS

Chile Patent Application No. 3274-2015 second Office Action dated Jan. 22, 2018.
(Continued)

*Primary Examiner* — Bethany P Barham
*Assistant Examiner* — Barbara S Frazier
(74) *Attorney, Agent, or Firm* — Wilson Sonsini Goodrich & Rosati

(57) ABSTRACT

An antiseptic composition suitable for use on skin and wounds comprising a source of an antimicrobial agent and an agent which disrupts biofilms. More, particularly the invention relates to a composition capable of providing effective antimicrobial activity while at the same time avoiding wound and skin irritation and retardation of wound healing.

7 Claims, 3 Drawing Sheets

Related U.S. Application Data continuation of application No. 11/610,671, filed on Dec. 14, 2006, now Pat. No. 9,149,035.

(51) Int. Cl.
| | | |
|---|---|---|
| *A61K 33/18* | (2006.01) | |
| *A01N 37/44* | (2006.01) | |
| *A01N 59/00* | (2006.01) | |
| *A01N 59/12* | (2006.01) | |
| *A01N 59/16* | (2006.01) | |
| *A61L 26/00* | (2006.01) | |

(52) U.S. Cl.
CPC ............ *A01N 59/16* (2013.01); *A61K 31/198* (2013.01); *A61K 33/18* (2013.01); *A61L 26/0004* (2013.01); *A61L 26/0066* (2013.01); *A61L 2300/104* (2013.01); *A61L 2300/106* (2013.01); *A61L 2300/11* (2013.01); *A61L 2300/206* (2013.01); *A61L 2300/212* (2013.01)

(56) References Cited

U.S. PATENT DOCUMENTS

| | | |
|---|---|---|
| 3,061,469 A | 10/1962 | Manowitz et al. |
| 3,092,552 A | 6/1963 | Romans |
| 4,258,056 A | 3/1981 | Lentsch |
| 4,612,337 A | 9/1986 | Fox, Jr. et al. |
| 4,655,758 A | 4/1987 | Ring et al. |
| 4,728,323 A | 3/1988 | Matson |
| 4,829,129 A | 5/1989 | Kelley |
| 4,889,654 A | 12/1989 | Mason et al. |
| 4,906,100 A | 3/1990 | Rice et al. |
| 4,973,848 A | 11/1990 | Kolobanov et al. |
| 5,064,652 A | 11/1991 | Bay |
| 5,326,567 A | 7/1994 | Capelli |
| 5,340,924 A | 8/1994 | Tomita et al. |
| 5,407,656 A | 4/1995 | Roozdar |
| 5,527,534 A | 6/1996 | Myhling |
| 5,567,495 A | 10/1996 | Modak et al. |
| 5,616,347 A | 4/1997 | Alliger et al. |
| 5,662,913 A | 9/1997 | Capelli |
| 5,709,870 A | 1/1998 | Yoshimura et al. |
| 5,731,083 A | 3/1998 | Bahia et al. |
| 5,744,151 A | 4/1998 | Capelli |
| 5,744,155 A | 4/1998 | Friedman et al. |
| 5,762,620 A | 6/1998 | Cartmell et al. |
| 5,820,918 A | 10/1998 | Ronan et al. |
| 5,848,995 A | 12/1998 | Walder |
| 5,860,947 A | 1/1999 | Stamler |
| 5,998,488 A | 12/1999 | Shinohara et al. |
| 6,075,177 A | 6/2000 | Bahia et al. |
| 6,207,601 B1 | 3/2001 | Maurer et al. |
| 6,290,496 B1 | 9/2001 | Azar et al. |
| 6,413,556 B1 | 7/2002 | Bathurst et al. |
| 6,468,965 B1 | 10/2002 | Cutler |
| 6,548,730 B1 | 4/2003 | Patel et al. |
| 6,555,508 B1 | 4/2003 | Paul et al. |
| 6,605,751 B1 | 8/2003 | Gibbins et al. |
| 6,669,981 B2 | 12/2003 | Parsons et al. |
| 6,750,262 B1 | 6/2004 | Haehnle et al. |
| 6,753,063 B1 | 6/2004 | Pung et al. |
| 7,033,511 B2 | 4/2006 | Zawada et al. |
| 7,267,828 B2 | 9/2007 | Parsons et al. |
| 8,637,072 B2 | 1/2014 | Kershaw et al. |
| 9,149,035 B2 | 10/2015 | Percival et al. |
| 2002/0091074 A1 | 7/2002 | Wooley et al. |
| 2002/0160941 A1 | 10/2002 | Kruzel |
| 2002/0172709 A1 | 11/2002 | Nielsen et al. |
| 2002/0183808 A1 | 12/2002 | Biel |
| 2003/0180345 A1 | 9/2003 | Hill et al. |
| 2003/0180346 A1 | 9/2003 | Woods |
| 2004/0001880 A1 | 1/2004 | Bowler et al. |
| 2004/0247652 A1 | 12/2004 | Sabesan |
| 2005/0059731 A1 | 3/2005 | Albrecht et al. |
| 2006/0019571 A1 | 1/2006 | Lange et al. |
| 2006/0051385 A1* | 3/2006 | Scholz ................... A61K 31/14 424/405 |
| 2006/0051430 A1 | 3/2006 | Arata et al. |
| 2006/0115440 A1 | 6/2006 | Arata et al. |
| 2006/0234959 A1 | 10/2006 | Biel et al. |
| 2006/0254988 A1 | 11/2006 | Frampton |
| 2007/0042024 A1 | 2/2007 | Gladman et al. |
| 2007/0134136 A1 | 6/2007 | Polyakov et al. |
| 2007/0166399 A1 | 7/2007 | Burton et al. |
| 2007/0255192 A1 | 11/2007 | Patel et al. |
| 2008/0112920 A1 | 5/2008 | Chia et al. |
| 2008/0188558 A1 | 8/2008 | Godal et al. |
| 2008/0226724 A1 | 9/2008 | Ji et al. |
| 2009/0012440 A1 | 1/2009 | Bray et al. |
| 2009/0177135 A1 | 7/2009 | Rogers et al. |
| 2010/0015208 A1 | 1/2010 | Kershaw et al. |
| 2010/0113537 A1 | 5/2010 | Nonaka |
| 2010/0129633 A1 | 5/2010 | Law |
| 2010/0310845 A1 | 12/2010 | Bond et al. |
| 2011/0117025 A1 | 5/2011 | Dacosta et al. |
| 2011/0237994 A1 | 9/2011 | Russ et al. |
| 2011/0319808 A1 | 12/2011 | Bowler et al. |
| 2012/0202398 A1 | 8/2012 | Marshall et al. |
| 2016/0101207 A1 | 4/2016 | Parsons et al. |
| 2017/0347661 A1 | 12/2017 | Parsons |

FOREIGN PATENT DOCUMENTS

| | | |
|---|---|---|
| CN | 105407930 A | 3/2016 |
| EP | 0616650 A1 | 9/1994 |
| EP | 0680344 A1 | 11/1995 |
| EP | 1158859 A1 | 12/2001 |
| EP | 1318842 A1 | 6/2003 |
| EP | 1343510 A1 | 9/2003 |
| EP | 1425050 A1 | 6/2004 |
| EP | 1557088 A1 | 7/2005 |
| EP | 1882482 A2 | 1/2008 |
| EP | 1925719 A1 | 5/2008 |
| EP | 1925917 A1 | 5/2008 |
| EP | 1343510 B1 | 5/2010 |
| EP | 2262545 A2 | 12/2010 |
| EP | 2996730 A1 | 3/2016 |
| EP | 3241439 A1 | 11/2017 |
| FR | 2604900 A1 | 4/1988 |
| GB | 735462 A | 8/1955 |
| GB | 1105829 A | 3/1968 |
| GB | 2094802 A | 9/1982 |
| GB | 2220881 A | 1/1990 |
| JP | H07502081 A | 3/1995 |
| JP | H08505790 A | 6/1996 |
| JP | 2000510539 A | 8/2000 |
| JP | 2002539140 A | 11/2002 |
| JP | 2003510475 A | 3/2003 |
| JP | 2003512095 A | 4/2003 |
| JP | 2003531828 A | 10/2003 |
| JP | 2007509034 A | 4/2007 |
| JP | 2007167266 A | 7/2007 |
| JP | 2007532606 A | 11/2007 |
| JP | 2008502735 A | 1/2008 |
| JP | 2008038293 A | 2/2008 |
| JP | 2008503557 A | 2/2008 |
| JP | 2008507327 A | 3/2008 |
| JP | 2008526997 A | 7/2008 |
| JP | 2009519312 A | 5/2009 |
| JP | 2016040294 A | 3/2016 |
| JP | 2016519966 A | 7/2016 |
| RU | 2092180 C1 | 10/1997 |
| WO | WO-8401721 A1 | 5/1984 |
| WO | WO-9218098 A1 | 10/1992 |
| WO | WO-9312275 A1 | 6/1993 |
| WO | WO-9319152 A1 | 9/1993 |
| WO | WO-9402022 A1 | 2/1994 |
| WO | WO-9416746 A1 | 8/1994 |
| WO | WO-9601119 A1 | 1/1996 |
| WO | WO-9702313 A1 | 1/1997 |
| WO | WO-9806260 A1 | 2/1998 |
| WO | WO-9846818 A1 | 10/1998 |
| WO | WO-0054593 A1 | 9/2000 |

(56) References Cited

FOREIGN PATENT DOCUMENTS

| | | |
|---|---|---|
| WO | WO-0072874 A1 | 12/2000 |
| WO | WO-0123653 A1 | 4/2001 |
| WO | WO-0124839 A1 | 4/2001 |
| WO | WO-0128338 A2 | 4/2001 |
| WO | WO-0128600 A1 | 4/2001 |
| WO | WO-0137936 A1 | 5/2001 |
| WO | WO-0162289 A2 | 8/2001 |
| WO | WO-0243743 A1 | 6/2002 |
| WO | WO-02055060 A2 | 7/2002 |
| WO | WO-02078755 A2 | 10/2002 |
| WO | WO-03022317 A1 | 3/2003 |
| WO | WO-03047341 A2 | 6/2003 |
| WO | WO-03068247 A1 | 8/2003 |
| WO | WO-2004028461 A2 | 4/2004 |
| WO | WO-2004035718 A2 | 4/2004 |
| WO | WO-2004056346 A1 | 7/2004 |
| WO | WO-2004108093 A2 | 12/2004 |
| WO | WO-2005020915 A2 | 3/2005 |
| WO | WO-2005032459 A2 | 4/2005 |
| WO | WO-2005079582 A1 | 9/2005 |
| WO | WO-2005099757 A1 | 10/2005 |
| WO | WO-2005123103 A1 | 12/2005 |
| WO | WO-2006000765 A1 | 1/2006 |
| WO | WO-2006015317 A2 | 2/2006 |
| WO | WO-2006022970 A1 | 3/2006 |
| WO | WO-2006029213 A2 | 3/2006 |
| WO | WO-2006111624 A2 | 10/2006 |
| WO | WO-2007005720 A2 | 1/2007 |
| WO | WO-2007068938 A2 | 6/2007 |
| WO | WO-2008035734 A1 | 3/2008 |
| WO | WO-2009130608 A2 | 10/2009 |
| WO | WO-2010070292 A1 | 6/2010 |
| WO | WO-2012061225 A2 | 5/2012 |
| WO | WO-2012072980 A1 | 6/2012 |
| WO | WO-2012136968 A1 | 10/2012 |
| WO | WO-2014186590 A1 | 11/2014 |

OTHER PUBLICATIONS

Japan Patent Application No. 2016-514095 Office Action dated Feb. 20, 2018.
Kryukov et al., The role of bacteriological examination in diagnosis of chronic tonsillitis. Вестнк 3:35-38, 2008.
European Patent Application No. 12719420.7 Examination Report dated Apr. 5, 2017.
Saudi Arabia Patent Application No. 515370133 2nd Examination Report dated Feb. 6, 2017.
Chinese Patent Application No. 201480028155.4 First Office Action dated Apr. 18, 2017 (no translation provided to date).
510(k) Premarket Notification, Aquacel and Aquacel Ag, Section 5: 510(k) Summary revised Apr. 21, 2008, 6 pages.
Banin et al., Chelator-induced dispersal and killing of Pseudomonas aeruginosa cells in a biofilm. Applied and Environmental Microbiology, 72(3):2064-2069, 2006.
Bowler et al., Dressing conformability and silver-containing wound dressings. Wounds U.K., 6:14-20 (2010).
Canadian Patent Application No. 2,745,059 Office Action dated Oct. 25, 2016.
Capinera et al., Insectional activity of photoactive dyes to American and migratory grasshoppers (*Orthoptera acrididae*). J.Econ. Entomol., 92(3):662-666, 2000.
Ceri et al., The Calgary biofilm device: New technology for rapid determination of antibiotic susceptibilities of bacterial biofilms. Journal of Clinical Microbiology, 37(6):1771-1776, 1999.
Chemburu et al., Light-induced biocidal action of conjugated polyelectrolytes supported on colloids Langmuir, 24:11053-11062 (2008).
Chinese Patent Application No. 201180066375.2 Office Action dated Sep. 26, 2016.
Chinese Patent Application No. 201280027537.6 Chinese Third Office Action dated Mar. 2, 2016.
Chinese Patent Application No. 201280027537.6 Office Action dated Sep. 12, 2016.
Demidova and Hamblin, Photodynamic therapy targeted to pathogens Int. J. Immunopathol Pharmacol., 17(3):245-254, 2004.
Dougherty et al., Photodynamic therapy. Journal of the National Cancer Institute, 90(12): 889-905, 1998.
European Patent Application No. 09795521.5 Communication dated Mar. 24, 2017.
European Patent Application No. 12719420.7 Communication dated Jul. 20, 2016.
FDA website on Medical Devices, Premarket Notification (510k), 4 pages, 2013.
Harrison-Balestra et al., A wound isolated *Pseudomonas aeruginosa* grows a biofilm in vitro within 10 hours and is visualized by light microscopy. Dermatol. Surgery, 29(6):631-635, 2003.
Japanese Patent Application No. 2013-541415 Final Rejection dated Jun. 14, 2016.
Japanese Patent Application No. 2014-242257 Office Action dated Apr. 5, 2016.
Japanese Patent Application No. 2014-543972 Office Action dated Dec. 20, 2016.
Japanese Patent Application No. 2015-200279 Office Action dated Jul. 12, 2016.
Jones et al., Antimicrobial activity of silver-containing dressings is influenced by dressing conformability with a wound surface. Wounds, 17:263-270 (2005).
JP-A-H7-504699 (English counterpart WO93/19152).
JP-A-H7-509236 (English counterpart WO94/02022).
Kapoor et al., Fluorescence and absorption spectra of Rose-Bengal dye in the presence of surfactants. Journal of Luminescence, 22(4):429-439, 1981. (Abstract only).
Mexican Patent Application No. MX/a/2013/006090 Official Action dated Jun. 7, 2016.
Nagai et al., Suppressive effects of EDTA for Pseudomonas aeruginosa products biofilm. Gifu Daigaku Igakubu Kiyo, 44(1):193-200, 1996. Retrieved from Chemical Abstracts, 125(19), p. 628.
Ovington, The Value of Silver in Wound Management. Podiatry Today, Dec. 1999, 12(7):59-62. (marked as Exhibit 3 at the Deposition of Fiona Adam).
Parikh et al., Antimicrobial silver/sodium carboxymethyl cotton dressings for burn wounds Textile Research Journal, 75(2):134-138 (2005).
PCT/GB2012/000329 International Search Report and Written Opinion dated Jul. 17, 2012.
PCT/US2014/038224 International Preliminary Report on Patentability dated Nov. 17, 2015.
PCT/US2014/038224 International Search Report dated Sep. 15, 2014.
PCT/US2014/038224 Written Opinion dated Sep. 15, 2014.
PCT/GB2009/002912 International Preliminary Report on Patentability dated Jun. 21, 2011.
PCT/GB2009/002912 International Search Report and Written Opinion dated Mar. 2, 2010.
PCT/GB2011/001665 International Preliminary Report on Patentability dated Jun. 4, 2013.
PCT/GB2011/001665 International Search Report dated Mar. 2, 2012.
PCT/GB2011/001665 Written Opinion dated Mar. 2, 2012.
Ramage et al., Inhibition on Candida albicans biofilm formation using divalent cation chelators (EDTA), Mycopathologia, 164:301-306, 2007.
Russian Patent Application No. 2013129866 Official Action dated Oct. 21, 2016.
Russian Patent Application No. 2013149176 Official Action dated Jun. 2, 2016.
Russian Patent Application No. 2015153446 Office Action dated Feb. 10, 2016 (in Russian).
Senter, A Textbook of Organic Chemistry, Fifth Ed. 1919, pp. 435-443.
Smith and Nephew, OTC medication information: Dermal wound cleanser—benzethonium chloride spray Dec. 17, 2009, p. 1-6. XP55031919.

(56) References Cited

OTHER PUBLICATIONS

Tallardia. Drug synergism: Its detection and applications. The Journal of Pharmacology and Experimental Therapeutics, 298(3):865-872, 2001.

Thomas and McCubbin, An in vitro analysis of the antimicrobial properties of 10 silver-containing dressings. The Journal of Wound Care, Sep. 2003, 12(8):105-108.

U.S. Appl. No. 13/990,755 Office Action dated Jan. 19, 2017.
U.S. Appl. No. 09/997,545 Office Action dated Feb. 10, 2003.
U.S. Appl. No. 09/997,545 Office Action dated Jul. 3, 2002.
U.S. Appl. No. 10/734,784 Office Action dated Apr. 4, 2007.
U.S. Appl. No. 11/610,671 Office Action dated Apr. 2, 2008.
U.S. Appl. No. 11/610,671 Office Action dated Apr. 7, 2011.
U.S. Appl. No. 11/610,671 Office Action dated Aug. 17, 2009.
U.S. Appl. No. 11/610,671 Office Action dated Dec. 3, 2008.
U.S. Appl. No. 11/610,671 Office Action dated Feb. 18, 2010.
U.S. Appl. No. 11/610,671 Office Action dated Mar. 11, 2015.
U.S. Appl. No. 11/610,671 Office Action dated Mar. 20, 2014.
U.S. Appl. No. 11/610,671 Office Action dated Oct. 20, 2011.
U.S. Appl. No. 11/610,671 Office Action dated Oct. 8, 2014.
U.S. Appl. No. 11/610,671 Office Action dated Sep. 12, 2013.
U.S. Appl. No. 12/406,316 Office Action dated Apr. 4, 2012.
U.S. Appl. No. 12/406,316 Office Action dated Apr. 5, 2013.
U.S. Appl. No. 12/406,316 Office Action dated Aug. 10, 2011.
U.S. Appl. No. 12/406,316 Office Action dated Nov. 26, 2012.
U.S. Appl. No. 13/124,472 Office Action dated Feb. 16, 2016.
U.S. Appl. No. 13/124,472 Office Action dated Jan. 18, 2013.
U.S. Appl. No. 13/124,472 Office Action dated Jun. 21, 2013.
U.S. Appl. No. 13/124,472 Office Action dated Jun. 4, 2015.
U.S. Appl. No. 13/124,472 Office Action dated Oct. 3, 2014.
U.S. Appl. No. 13/990,755 Office Action dated May 5, 2016.
U.S. Appl. No. 14/889,818 Office Action dated Sep. 27, 2016.
U.S. Appl. No. 14/114,517 Office Action dated Apr. 23, 2015.
U.S. Appl. No. 14/114,517 Office Action dated Aug. 13, 2015.
U.S. Appl. No. 14/114,517 Office Action dated Mar. 24, 2016.
U.S. Appl. No. 14/114,517 Office Action dated Oct. 20, 2016.

Wainwright. Photodynamic antimicrobial chemotherapy (PACT). Journal of Antimicrobial Chemotherapy, 42:13-28, 1998.
Wainwright et al., The Use of new methylene blue in Pseudomonas aeruginosa biofilm destruction. Biofouling, 18:247-249, 2002. (Abstract only).
White "An historical overview of the use of silver in wound management," Actisorb Silver 220, The Silver Supplement Part Two: Clinical Evidence, 6(Supp. Pt. 2): 6 pages (2001).
Chinese Patent Application No. 201180066375.2 Reexamination Decision dated Dec. 20, 2017.
U.S. Appl. No. 14/889,818 Office Action dated Jan. 10, 2018.
Database Biosis, Biosciences Information Service, Philadelphia, PA, 1992, Kida N., et al., "Effect of PH on Preferential Antibacterial Activity of Ethylenediaminetetraacetic Acid EDTA", 1 page. XP002485724, Database Accession No. PREV199294118093.
Database Biosis, Biosciences Information Service, Philadelphia, PA, 2005, Percival, L, etal., "Tetrasodium EDTA as a novel central venous catheter lock solution against biofilm", 1 page. XP002485725, Database Accession No. PREV200600021247.
Database CA, Chemical Abstracts Service, Columbus, Ohio, US; 1979, Izzat, I.N., et al., "Effect of varying concentrations of EDTA on the antimicrobial properties of cutting fluid preservatives", 1 page. XP002485722, STN-International Database Accession No. 93:62380.
Database CA, Chemical Abstracts Service, Columbus, Ohio, US; 1969, Reybrouck, G., et al., "Effect of ethylenediaminetetraacetate on the germicidal action of disinfectants against Pseudomonas aeruginosa", 1 page. XP002485721, STN-International Database Accession No. 72:11588.
Database Medline, US National Library of Medicine, Bethesda, MD, 1988, Kaur, P., et al., "Effect of certain chelating agents on the antibacterial action of silver nitrate", 1 page. XP002485723, Database Accession No. NLM3143759.

European Patent Application No. EP 06820530.1 Communication dated Apr. 7, 2016.
European Patent Application No. EP 06820530.1 Communication dated Jan. 30, 2013.
European Patent Application No. EP 06820530.1 Communication dated Mar. 30, 2009.
Gilbert, et al., The Use of Poloxamer Hydrogels for the Assessment of Biofilm Susceptibility Towards Biocide Treatments, Journal of Applied Microbiology, 85:985-990, 1998.
Kaur et al., Effect of certain chelating agents on the antibacterial action of silver nitrate. Journal of Hygiene, Epidemiology, Microbiology and Immunology. 32(3):299-306, 1988.
Lineaweaver, et al., Topical Antimicrobial Toxicity, Arch Surg., 120:267-270, 1985.
Muller et al. pH-dependent formation of ethylenediaminetetraacetic acid supramolecular aggregates. FEBS Lett 340:17-21 (1994).
PCT/GB2006/004691 International Preliminary Report on Patentability dated Aug. 12, 2008.
PCT/GB2006/004691 International Search Report dated Jul. 7, 2008.
PCT/GB2006/004691 Written Opinion dated Jul. 7, 2008.
Pennington, Jean, A Review of Iodine Toxicity Reports, Journal of the American Dietetic Association, 90:1571-1581, 1990.
Percival et al., Tetrasodium EDTA as a novel central venous catheter lock solution against biofilm. Infection Control and Hospital Epidemiology, 26(6):515-519, 2005.
Poon, et al., In Vitro Cytoxicity of Silver: Implication for Clinical Wound Care, Burns, 230:140-147, 2004.
Reybrouck et al., Effect of ethylenediamine tetraacetate on the germicidal action of disinfectants against "Pseudomona." Acta Clinica Belgica, 24(1):32-41, 1969.
U.S. Appl. No. 14/795,176 Office Action dated Feb. 3, 2016.
Wirtanen, et al., Performance Evaluation of disinfectant Formulations Using Poloxamer-hydrogel Biofilm-constructs, Journal of Applied Microbiology, 85:965-971, 1998.
Canadian Patent Application No. 2819303 Office Action dated Oct. 24, 2017.
Chinese Patent Application No. 201280027537.6 Decision of Reexamination dated Oct. 27, 2017.
Japanese Patent Application No. 2015-200279 Office Action dated Aug. 31, 2017.
Arata, J. *Staphylococcus aureus* and the skin. Japanese Journal of Chemotherapy, 49(3):147-156, 2001.
Canadian Patent Application No. 2,745,059 Office Action dated Aug. 2, 2017.
Chile Patent Application No. 3274-2015 Office Action dated Jun. 20, 2017.
Chinese Patent Application No. 201180066375.2 Reexamination Notice dated Jul. 3, 2017.
Chinese Patent Application No. 201280027537.6 Reexamination Notice dated Jun. 8, 2017.
European Patent Application No. 17163418.1 extended European Search Report dated Sep. 17, 2017.
Japanese Patent Application No. 2014-242257 Office Action dated May 23, 2017.
Japanese Patent Application No. 2016-154639 Office Action dated Jun. 8, 2017.
Japanese Patent Application No. 2016-202835 Office Action dated Jun. 20, 2017.
Ono, N. A Semi-quantitative measurement of glycocalyx and an ATP bioluminescent assay for the analysis of Pseudomonas Aeruginosa biofilm. The Japanese Journal of Urology, 86(9):1440-1449, 1995.
Russian Patent Application No. 2013129866/10 Protocol of a Meeting with the Examiner dated Jun. 14, 2017.
Sharma et al., Toluidine blue-mediated photodynamic effects on Staphylococcal biofilms. Antimicrobial Agents and Chemotherapy, 52(1):299-305, 2008.
U.S. Appl. No. 13/990,755 Office Action dated Jun. 29, 2017.
U.S. Appl. No. 14/889,818 Office Action dated Jun. 9, 2017.
Usacheva et al., Interaction of the photobactericides methylene blue and toluidine blue with a fluorophore in Pseudomonas aeruginosa cells. Lasers in Surgery and Medicine, 40:55-61, 2008.

(56) References Cited

OTHER PUBLICATIONS

Wood et al., Erythrosine is a potential photosensitizer for the photodynamic therapy of oral plaque biofilms. Journal of Antimicrobial Chemotherapy, 57:680-684, 2006.
Japanese Patent Application No. 2015-200279 Office Action dated Feb. 7, 2017.
Kita et al., pH-Dependent preferential antibacterial activity of Ethylenediaminetetraacetic acid (EDTA). Japanese Journal of Bacteriology, 47(4):6 pages, 1992.
European Patent Application No. 14797983.5 Supplementary European Search Report dated Dec. 6, 2016.
Saudi Arabia Patent Application No. 515370133 Examination Report dated Oct. 18, 2016.
U.S. Appl. No. 14/889,818 Office Action dated Jan. 25, 2017.
Australian Patent Application No. 2017201084 Examination Report No. 1 dated May 18, 2018.
Australian Patent No. 2014265336 Second Examination Report dated Mar. 26, 2018.
Canadian Patent Application No. 2,745,059 Office Action dated Apr. 20, 2018.
European Patent Application No. 09795521.5 Office Action dated May 9, 2018.
India Patent Application No. 9392/DELNP/2013 First Examination Report dated Feb. 23, 2018.
Japan Patent Application No. 2017-112806 Official Action dated Mar. 6, 2018.
Japanese Patent Application No. 2016-202835 Office Action dated Mar. 6, 2018.
Mexican Patent Application No. MX/a/2015/015197 Office Action dated Mar. 2, 2018.
Russian Patent Application No. 2013149176 Official Action dated Feb. 21, 2018.
Swisher, R.D., Surfactant effects on humans and other mammals. The Soap and Detergent Association, Scientific and Technical Report, 4:1-8, 11, 16, 17,19, Nov. 1966.
Taiwanese Application No. 103117207 Office Action dated Apr. 11, 2018.
U.S. Appl. No. 14/889,818 Office Action dated Jun. 19, 2018.
U.S. Appl. No. 13/990,755 Office Action dated Apr. 5, 2018.
Varani et al., Human skin in organ culture and human skin cells (keratinocytes and fibroblasts) in monolayer culture for assessment of chemically induced skin damage. Toxicol Pathol., 35(5):693-701, 2007.
Vengerovsky, A.I., Pharmaceutical incompatibility. Bulletin of Siberian Medicine, 3:12 pages, 2003. http.7/old.ssmu.ru/bull/03/3/1684.pdf.
AMR: a major European and Global challenge: fact sheet. Antimicrobial Resistance—European Commission (EC-AMR) Sep. 8, 2017. https://ec.europa.eu/health/amr/sites/amr/files/amr_factsheet_en.pdf. Accessed Jul. 2, 2018.
Anwar H, Dasgupta M, Costerton J. Testing the susceptibility of bacteria in biofilms to antibacterial agents. Antimicrob Agents Chemother. 1990; 34: 2043-2046.
Australian Patent Application No. 2013366038 Examination Report No. 2 dated Jun. 19, 2018.
Bay L, Kragh K, Eickhardt S, et al. Bacterial aggregates establish at the edges of acute epidermal wounds. Adv Wound Care. 2018; 7: 105-13.
Bohn G, Liden B, Schultz G, et al. Ovine-based collagen matrix dressing: Next-generation collagen dressing for wound care. Adv Wound Care. 2016; 5: 1-10.
Bowler P. Antibiotic resistance and biofilm tolerance: a combined threat in the treatment of chronic infections. J Wound Care. 2018 27: 273-277.
Bowler P, Jones S, Davies B, Coyle E. Infection control properties of some wound dressings. J Wound Care. 1999; 8: 499-502.
Bowler P, Jones S, Towers V, et al. Dressing conformability and silver-containing wound dressings. Wounds UK. 2010; 6: 14-20.

Bowler P, Parsons D. Combatting wound biofilm and recalcitrance with a novel anti-biofilm Hydrofiber® wound dressing. Wound Medicine. 2016; 14: 6-11.
Bryant R, Nix D. Principles for practice development to facilitate outcomes and productivity. In Bryant R and Nix D, eds. Acute and Chronic Wounds: Current Management Concepts. 5th ed. St. Louis, MO: Elsevier; 2016: 1-20.
Canadian Patent Application No. 2,834,871 Office Action dated Jan. 31, 2018.
Cavaliere R, Ball J, Turnbull L, Whitchurch C. The biofilm matrix destabilizers, EDTA and DNaseI, enhance the susceptibility of nontypeable Hemophilus influenzae biofilms to treatment with ampicillin and ciprofloxacin. Microbiology. 2014; 3: 557-67.
Centers for Disease Control and Prevention. Antibiotic Resistance Threats in the United States. 2013. http://www.cdc.gov/drugresistance/threat-report-2013/pdf/ar-threats-2013-508.pdf. Accessed Aug. 1, 2018.
Chan B, Cadarette S, Wodchis W, Wong J, Mittmann N, Kran M. Cost-of-illness studies in chronic ulcers: A systemic review. J Wound Care. 2017; 26: S4-S15.
Chinese Patent Application No. 201380073403.2 Third Office Action dated Mar. 26, 2018.
Ciofu O, Rojo-Molinero E, Macia M, Oliver A. Antibiotic treatment of biofilm infections. APMIS. 2017; 125: 304-19.
Costerton J, Geesey G, Cheng K. How bacteria stick. Sci Am. 1978; 238: 86-95.
Costerton J, Irvin R, Cheng K. The bacterial glycocalyx in nature and disease. Ann Rev Microbiol. 1981; 35: 299-324.
Costerton J, Stewart P, Greenberg E. Bacterial biofilms: a common cause of persistent infections. Science. 1999; 284: 1318-22.
Costerton JW. Bacterial biofilms in nature and disease. Ann Rev Microbiol. 1987; 41: 435-64.
Dini V, Salvo P, Janowska A, Di Francesco F, Barbini A, Romanelli M. Correlation between wound temperature obtained with an infrared camera and clinical wound bed score in venous leg ulcers. Wounds. 2015; 27: 274-8.
Doughty D, Sparks B. Wound healing physiology and factors that affect the wound repair process. In Bryant R and Nix D, eds. Acute and Chronic Wounds: Current Management Concepts. 5th ed. St. Louis, MO: Elsevier; 2016: 63-81.
Eming S, Martin P, Tomic-Canic M. Wound repair and regeneration: mechanisms, signaling, and translation. Sci Transl Med. 2014; 6: 57-72. doi: 10.1126/scitranslmed.3009337.
Etebu E, Arikekpar I. Antibiotics: Classification and mechanisms of action with emphasis on molecular perspective. Int J of Appl Microbiol and Biothech Res. 2016; 4: 90-101. http://www.bluepenjournals.org/ijambr/pdf/2016/October/Etebu_and_Arikekpar.pdf. Accessed Aug. 8, 2018.
European Centre for Disease Prevention and Control (ECDC). Proposals for EU Guidelines on the Prudent Use of Antimicrobials in Humans. Stockholm: ECDC; 2017. http://ecdc.europa.eu/en/publications/_layouts/forms/Publication_DispForm.aspx?List=4f55ad51-4aed-4d32-b960-af70113dbb90&ID=1643. Accessed Jul. 2, 2018.
European Patent Application No. 12719420.7 Examination Report dated Aug. 7, 2018.
European Patent Application No. 13821122.2 Communication dated Oct. 30, 2017.
Fife C, Carter M, Walker D, Thomson B. Wound care outcomes and associated cost among patients treated in US outpatient wound centers: Data from the US Wound Registry. Wounds. 2012; 24: 10-7.
Finnegan S, Percival S. EDTA: an antimicrobial and antibiofilm agent for use in wound care. Adv Wound Care. 2015; 4: 415-21.
Fleming D, Rumbaugh K. Approaches to dispersing medical biofilms. Microorganisms. 2017; 5: 1-16.
Frykberg R, Banks J. Challenges in the treatment of chronic wounds. Adv Wound Care. 2015; 4: 560-82.
Gardner S, Frantz R, Doebbeling B. The validity of the clinical signs and symptoms used to identify localized chronic wound infection. Wound Repair Regen. 2001; 9: 178-86.
Gardner S, Hillis S, Frantz R. Clinical signs of infection in diabetic foot ulcers with high microbial load. Biol Res Nurs. 2009; 11: 119-28.

(56) References Cited

OTHER PUBLICATIONS

Gilchrist M, Seaton R. Outpatient parenteral antimicrobial therapy and antimicrobial stewardship: challenges and checklists. J Antimicrob Chemother. 2015; 70: 965-70.

Gottrup F. A specialized wound-healing center concept: importance of a multidisciplinary department structure and surgical treatment facilities in the treatment of chronic wounds. Am J Surg. 2004; 187: S38-S43.

Gottrup F, Apelqvist J, Bjarnsholt T, et al. Antimicrobials and non-healing wounds: Evidence, controversies and suggestions—key messages. J Wound Care. 2014; 23: 477-8, 480, 482.

Guest JF, Vowden K. The health economic burden that acute and chronic wounds impose on an average clinical commissioning group/health board in the UK. J Wound Care. 2017; 26: 292-303.

Harding K, Szczepkowski M, Mikosiński J, et al. Safety and performance evaluation of a next-generation antimicrobial dressing in patients with chronic venous leg ulcers. Int Wound J. 2016; 13: 442-8.

Hobot et al., Effect of Hydrofiber wound dressings on bacterial ultrastructure. J Electron Microsc (Tokyo). 57(2):67-75 (2008).

Howell J, Stair T, Howell A, Mundt D, Falcone A, Peters S. The effect of scrubbing and irrigation with normal saline, povidone iodine, and cefazolin on wound bacterial counts in a Guinea pig model. Am J Emerg Med. 1993; 11: 134-38.

Hurlow J, Blanz E, Gaddy J. Clinical investigation of biofilm in non-healing wounds by high resolution microscopy techniques. J Wound Care. 2016; 25(suppl 9): S11-S22.

International Wound Infection Institute (IWII). Wound infection in clinical practice. Wounds International, 2016. http://www.woundinfection-institute.com/wp-content/uploads/2017/03/IWII-Wound-infection-in-clinical-practice.pdf. Accessed Jul. 2, 2018.

James G, Swogger E, Wolcott R, et al. Biofilms in chronic wounds. Wound Repair Regen. 2008; 16: 37-44.

Japanese Patent Application No. 2015-548762 Office Action dated Jul. 31, 2018.

Japanese Patent Application No. 2015-548762 Office Action dated Oct. 10, 2017.

Jasovský D, Littmann J, Zorzet A, Cars O. Antimicrobial resistance—a threat to the world's sustainable development. Upsala J Med Sci. 2016; 121: 159-64.

Johani K, Malone M, Jensen S, et al. Microscopy visualisation confirms multi-species biofilms are ubiquitous in diabetic foot ulcers. Int Wound J. 2017; 14: 1160-9.

Keast D, Swanson T, Carville K, Fletcher J, Schultz G, Black J. Ten top tips . . . understanding and managing wound biofilm. Wounds International. 2014; 5: 20-3.

Kim D, Namen W, Moore J, Buchanan M, Hayes V, Myntti, M, Hakaim A. Clinical assessment of a biofilm-disrupting agent for the management of chronic wounds compared with standard of care: a therapeutic approach. Wounds. 2018; 30: 120-30.

Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.

Lazarus G, Cooper D, Knighton D, Percoraro R, Rodeheaver G, Robson M. Definitions and guidelines for assessment of wounds and evaluation of healing. Wound Repair Regen. 1994; 2: 165-70.

Lewis K. Persister cells. Ann Rev Microbiol. 2010; 64: 357-72.

Lipsky B, Aragón-Sánchez J, Diggle M, et al. IWGDF guidance on the diagnosis and management of foot infections in persons with diabetes. Diabetes Metab Res Rev. 2016; 32: 45-74.

Lipsky B, Dryden M, Gottrup F, et al. Antimicrobial stewardship in wound care: A position paper from the British society for antimicrobial chemotherapy and European wound management association. J Antimicrob Chemother 2016; 71: 3026-35.

Lipsky B. Medical treatment of diabetic foot infections. Clin Infect Dis. 2004; 39: S104-S114.

Lipsky B, Peters E, Senneville E, et al. Expert opinion on the management of infections in the diabetic foot. Diabetes Metab Res Rev. 2012; 28(suppl 1): 163-78.

Macia M, Roho-Molinero E, Oliver A. Antimicrobial susceptibility testing in biofilm-growing bacteria. Clin Microbiol Infect. 2014; 20: 981-90.

Malone M, Bjarnsholt T, McBain A, et al. The prevalence of biofilms in chronic wounds: a systematic review and meta-analysis of published data. J Wound Care. 2017; 26: 20-5.

McDonnell G, Russell A. Antiseptics and disinfectants: Activity, action, and resistance. Clin Microbiol Rev. 1999; 12: 147-79.

Metcalf D, Bowler P. Biofilm delays wound healing: A review of the evidence. Burns Trauma. 2013; 1: 5-12.

Metcalf D, Bowler P, Parsons D. In: Dhanasekaran D, ed. Wound Biofilm and Therapeutic Strategies, Microbial Biofilms—Importance and Applications. Rijeka, Croatia: InTech; 2016. https://www.intechopen.com/books/microbial-biofilms-importance-and-applications/wound-biofilm-and-therapeutic-strategies. Accessed Aug. 8, 2018.

Metcalf D, Parsons D, Bowler P. A next-generation antimicrobial wound dressing: a real-life clinical evaluation in the UK and Ireland. J Wound Care. 2016; 25: 132-8.

Nagoba B, Suryawanshi N, Wadher B, Selkar S. Acidic environment and wound healing: a review. Wounds. 2015; 27: 5-11.

Newman G, Walker M, Hobot J, Bowler P. Visualisation of bacterial sequestration and bactericidal activity within hydrating Hydrofiber wound dressings. Biomaterials. 2006; 27: 1129-39.

Nickel J, Wright J, Ruseska I, Marrie T, Whitfield C, Costerton J. Antibiotic resistance of pseudomonas aeruginosa colonizing a urinary catheter in vitro. Eur J Clin Microbiol. 1985; 4: 213-18.

Nix D, Pierce B, Haugen V. Eliminating non-compliance. In Bryant R and Nix D, eds. Acute and Chronic Wounds: Current Management Concepts. 5th ed. St. Louis, MO: Elsevier; 2016: 428-40.

Nussbaum S, Carter M, Fife C, et al. An economic evaluation of the impact, cost, and Medicare policy implications of chronic nonhealing wounds. Value Health. 2018; 21: 27-32.

Olsen I. Biofilm-specific antibiotic tolerance and resistance. Eur J Clin Microbiol Infect Dis. 2015; 34: 877-86.

Parsons et al., Enhanced Performance and Mode of Action of a Novel Antibiofilm Hydrofiber Wound Dressing. BioMed Research International 2016: ID 7616471:1-14 (2016).

Percival S, Bowler P. Biofilms and their potential role in wound healing. Wounds. 2004; 16: 234-240.

Petchiappan A, Chatterji D. Antibiotic resistance: Current perspectives. ACS Omega 2017, 2, 7400-7409. https://www.researchgate.net/publication/321019969/download. Accessed Jul. 7, 2018.

Phillips T. Chronic cutaneous ulcers: Etiology and epidemiology. J Invest Dermatol. 1994; 102: 38S-41S.

Rhoads D, Wolcott R, Percival S. Biofilms in wounds: management strategies. J Wound Care. 2008; 17: 502-9.

Rodeheaver G, Ratliff C. Wound cleansing, wound irrigation, wound disinfection. In: Krasner D, van Rijswijk L, eds. Chronic Wound Care: The Essentials e-Book. Malvern, PA: HMP; 2018: 47-62. Available at: https://s3.amazonaws.com/whywoundcare/Files/Chapter+5.pdf. Accessed Jul. 7, 2018.

Romanelli M, Vowden K, Weir D. Exudate management made easy. Wounds International. 2014. http://www.woundsinternational.com/made-easys/view/exudate-management-made-easy-1. Accessed Jul. 11, 2018.

Rondas A, Schols J, Stobberingh E, Price P. Definition of infection in chronic wounds by Dutch nursing home physicians. Int Wound J. 2009; 6: 267-74.

Russian Patent Application 2015153446 Office Action and Search Report dated Apr. 23, 2018.

Said et al., An in vitro test of the efficacy of an anti-biofilm wound dressing.Int J Pharm. 474(1-2):177-181 (2014).

Savage V, Chopra I, ONeill A. *Staphylococcus aureus* biofilms promote horizontal transfer of antibiotic resistance. Antimicrob Agents Chemother. 2013; 57: 1968-70.

Sen C, Gordillo G, Roy S, et al. Human skin wounds: A major and snowballing threat to public health and the economy. Wound Repair Regen. 2009; 17: 763-71.

Seth A, Zhong A, Nguyen K, et al. Impact of a novel, antimicrobial dressing on in vivo, Pseudomonas aeruginosa wound biofilm: quantitative comparative analysis using a rabbit ear model. Wound Repair Regen. 2014; 22: 712-9.

(56) References Cited

OTHER PUBLICATIONS

Shanmugam V, Couch K, McNish S, Amdur R. Relationship between opioid treatment and rate of healing in chronic wounds. Wound Repair Regen. 2017; 25: 120-30.
Song T, Duperthuy M, Nyunt-Wai, S.Sub-optimal treatment of bacterial biofilms. Antibiotics. 2016; 5: 1-18.
Spellberg B, Srinivasan A, Chambers H. New societal approaches to empowering antibiotic stewardship. JAMA. 2016; 315: 1229-30.
Stevens D, Bisno A, Chambers H, et al. Practice guidelines for the diagnosis and management of skin and soft tissue infections: 2014 update by the Infectious Diseases Society of America. Clin Infect Dis. 2014; 59: 147-59.
Stewart P. Antimicrobial tolerance in biofilms. Microbiol Spectrum. 2015; 3: 1-30. https://www.ncbi.nlm.nih.gov/pmc/articles/PMC4507308/pdf/nihms697879.pdf. Accessed Jul. 24, 2018.
Gardner S. Wound Bioburden. In Baranoski, S, Ayello, E. eds. Wound Care Essentials: Practice and Principles. Philadelphia, PA: Wolters Klower; 2004, pp. 91-116.
Thomas-Hess, C. Checklist for factors affecting wound healing. Adv Skin Wound Care. 2011; 24: 192.
Torkington-Stokes R, Metcalf D, Bowler P. Management of diabetic foot ulcers: valuation of case studies. Br J Nurs. 2016; 25: S27-S33.
Understanding biofilms. Bacteriality. Published online May 26, 2008. http://bacteriality.com/2008/05/biofilm/. Accessed Jul. 2, 2018.
United Nations. World Population Aging. New York. 2017. http://www.un.org/en/development/desa/population/publications/pdf/ageing/WPA2017_Highlights.pdf. Accessed Jul. 24, 2018.
U.S. Appl. No. 14/654,498 Office Action dated Jul. 27, 2017.
U.S. Appl. No. 14/654,498 Office Action dated May 3, 2018.
U.S. Appl. No. 14/654,498 Office Action dated Nov. 17, 2017.
Walker M, Bowler P, Cochrane C. In vitro studies to show sequestration of matrix metalloproteinases by silver-containing wound care products. Ostomy Wound Manage. 2007; 53: 18-25.
Walker M, Metcalf D, Parsons D, Bowler P. A real-life clinical evaluation of a next-generation antimicrobial dressing on acute and chronic wounds. J Wound Care. 2015; 24: 11-22.
Waring et al. Physico-chemical characterisation of carboxymethylated spun cellulose fibres. Biomaterials 22:903-912 (2001).
Webb R. A chronic case of confusion. J of Wound Care. 2017; 26: 421.
Wilkinson H, Stephenson C, Hardman M. Comparing the effectiveness of polymer debriding devices using a porcine wound biofilm model. Adv Wound Care. 2016; 5: 475-85.
Wolcott R. Biofilms cause chronic infections. J of Wound Care. 2017; 26: 423-5.
Wolcott R. Disrupting the biofilm matrix improves wound healing outcomes. J Wound Care. 2015; 24: 366-71.
Wolcott R, Rhoads D. A study of biofilm-based wound management in subjects with critical limb ischemia. J Wound Care. 2008; 17: 145-55.
Wolcott R, Sanford N, Gabrilska R, Oates J, Wilkinson, J, Rumbaugh K. Microbiota is a primary cause of pathogenesis of chronic wounds. J Wound Care. 2016; 25: Sup10: S33-S43.
Zölß C, Cech JD. Efficacy of a new multifunctional surfactant-based biomaterial dressing with 1% silver sulphadiazine in chronic wounds. Int Wound J. 2016; 13: 738-43. doi: 10.1111/iwj.12361.
Canadian Patent Application No. 2,834,871 Office Action dated Oct. 1, 2018.
European Patent Application No. 14797983.5 Examination Report dated Feb. 26, 2019.
Kharkevich, D.A., Pharmacology:Textbook. Geotar-Media, p. 66-71, 2006. (translation of relevant section).

* cited by examiner

ANTIMICROBIAL COMPOSITION

CROSS REFERENCE

This application is a continuation application of U.S. application Ser. No. 14/795,176, filed Jul. 9, 2015, which is a continuation of U.S. application Ser. No. 11/610,671, filed Dec. 14, 2006, now U.S. Pat. No. 9,149,035, issued Oct. 6, 2015, which claims the benefit of a foreign priority application, GB Application No. 0525504.7 filed on Dec. 14, 2005, both of which are incorporated by reference in its entirety.

This invention relates to an antimicrobial composition which can be applied to skin, wounds, cuts, abrasions or burns for the prevention or treatment of infections. More particularly, the invention relates to a composition capable of providing effective antimicrobial activity while at the same time avoiding wound and skin irritation and retardation of wound healing.

BACKGROUND OF THE INVENTION

Overuse of antibiotics and the associated increase in bacterial resistance is impacting the efficacy of antibiotics in the treatment of wound infection. Effective alternatives to antibiotics are thus desirable.

Topical antimicrobial materials, and preparations containing them, have long been recognized as playing an important part in minimizing the opportunity for skin and wound infections. Antiseptics are non-selective chemical agents that can be safe to use on living tissue. Molecular iodine, ionic silver and oxidizing agents, such as sodium hypochlorite and chlorine dioxide, have been recognized as antiseptic agents with effectiveness against a wide range of microorganisms. There are, however, several barriers to making an effective antimicrobial composition for application to wounds based on such agents. One problem is that these antiseptic agents tend to react with organic materials found in the wound other than the intended microbial targets. This means that to be effective, antiseptic agents need to be included in treatment compositions at high levels, which may cause undesirable side effects with prolonged use such as cell toxicity, hypersensitivity reactions, skin staining and systemic effects. Such side effects are further described in "In vitro cytotoxity of silver: implication for clinical wound care". Poon V K, Burd A. Burns. 2004 March; 30(2):140-7, "A review of iodine toxicity reports". Pennington J A. J Am Diet Assoc. 1990 November; 90(11):1571-81 and "Topical antimicrobial toxicity". Lineaweaver W, Howard R, Soucy D, McMorris S, Freeman J, Crain C, Robertson J, Rumley T. Arch Surg. 1985 March; 120(3):267-70.

Wounds are often colonized by a variety of microorganisms, some of which may cause infection. It is increasingly recognized that microbial populations living within a biofilm environment contribute to delayed healing and infection. Biofilms are comprised of exopolymeric substances that are produced by bacteria once the bacteria attach to a surface, and this helps to protect microorganisms from immune cells and antimicrobial agents. Since efficacy of antimicrobial agents (e.g., antibiotics and antiseptics) is compromised by the biofilm matrix, strategies to disrupt the biofilm and expose microorganisms within can be helpful in increasing the activity level of antimicrobial agents and thus reduce the concentration of such agents needed to make an effective composition.

Ethylenediaminetetra-acetic acid (EDTA) added as the di-sodium or calcium di-sodium salts has been used to treat topical infections or to treat hard surfaces such as catheters. WO03/047341 describes the use of EDTA, for example, as an additive for a toothpaste. EDTA is also used as a formulation agent to reduce the effects of water hardness and, generally, as a chelating agent.

EDTA has been described in combination with other antibiotic agents. For example, in U.S. Pat. No. 5,998,488, EDTA is used in combination with an antimicrobial preservative in a solution for ophthalmic use. Formulations suitable for topical use on wounds have not been proposed.

There is, thus, a need for a composition which has the benefits of an antimicrobial agent but which reduces the potential of adverse reactions. Surprisingly, we have found that EDTA is capable of disrupting biofilms by chelating the metal ions, calcium and magnesium, that maintain the integrity of the biofilm matrix.

SUMMARY OF THE INVENTION

Accordingly, a first aspect of the invention provides an antimicrobial composition suitable for use on skin and wounds comprising a source of antiseptic agent and an agent which disrupts biofilms such as EDTA.

The presence of EDTA enhances the effect of the antiseptic so that the concentration of antiseptic agent may be reduced and yet still achieve effective antisepsis. By increasing the effectiveness of the antiseptic agent, its concentration in the composition can be reduced, thereby, reducing the potential for adverse reactions.

This aspect of the invention allows the preparation of compositions able to reduce the bacterial bioburden to a level manageable by the host within 24 hours using at least 50% less of the antiseptic agent, preferably 50-60% less, and, more preferably, 65-85% less. This then allows the wound to progress towards healing and can been evidenced by a visual improvement in the wound.

We have also found that it is possible to prepare a composition which includes EDTA which is effective under the conditions of pH normally found in a wound.

Accordingly, a second aspect of the invention provides a composition suitable for use on wounds comprising di-, tri- and tetra-basic salts of EDTA at a pH of 4 to 8.

DETAILED DESCRIPTION OF THE INVENTION

Figure 1:
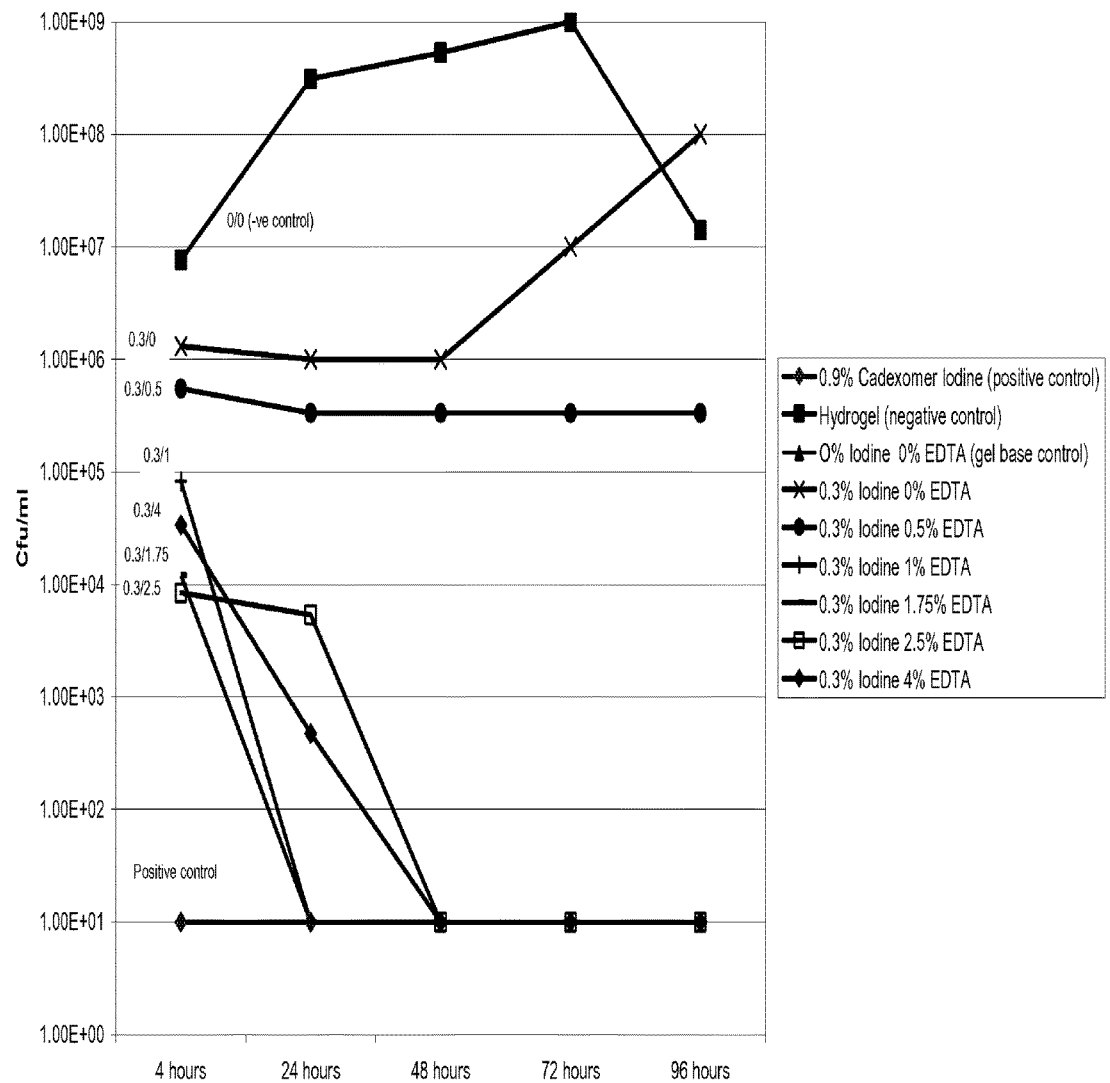
FIG. 1 is a graph showing the antimicrobial activity of a two component iodine generating solution with and without EDTA against *Staphylococcus aureus*.

The compositions according to a first aspect of the invention comprise an antiseptic agent, preferably molecular iodine, ionic silver, chlorhexidine, or hydrochloric acid or an oxidizing agent such as sodium hypochlorite, chlorine dioxide, hydrogen peroxide or peroxy acid salts. The antiseptic agent is preferably included in the composition at a level of from 0.01% to 10% by weight, more preferably 0.1% to 5% by weight. Iodine is preferably included in the composition at a level of from 0.01% to 10% by weight and more preferably from 0.1% to 1.0% by weight. Preferably, the source of iodine is an iodide and the composition further comprises an oxidant and a buffer, the oxidant being held separately from the iodide until the point of use. The buffer is preferably capable of maintaining the pH of the composition at between 4.5 and 6 so that iodine is generated at a physiologically acceptable and efficacious rate. Compositions comprising iodide and an oxidant held separately from the iodide are described further in EP1158859B.

Where iodide is present, the amount of oxidant in the composition is tailored to provide a stoichiometric match with iodide. Preferably, the oxidant is iodate and is provided in a molar ratio of from 1:4 to 1:10 with iodide. In this way, the iodide present in the composition fully reacts with the oxidant. Iodide and iodate are preferably present as sodium salts although other usual counter ions may be present.

Where the antiseptic agent is ionic silver, it is preferably included in the 10 composition at a level of from 0.1% to 10% by weight and more preferably 0.5% to 1.5% by weight.

The pH of the composition is generally below 8 and preferably between 4 and 8, more preferably between 4 and 6 and most preferably between 4.5 and 5.5. The desired pH may be achieved by incorporating buffering agents in the composition. Examples of buffering agents which may be included are citric acid/di-sodium hydrogen phosphate, citric acid/sodium citrate, acetic acid/sodium acetate. The buffering agent may conveniently be present in an amount of about 1% to 20% by weight of the composition, preferably about 4% to 6% by weight and more preferably about 5% by weight so as to provide an isotonic composition EDTA is preferably present as the di-, tri- or tetra-basic salts of EDTA. We have found that these salts are effective for eradicating microorganisms in the free floating or planktonic state and biofilm state alone or in the presence of an antiseptic agent. For example, we have found that EDTA at concentrations of 0.1-40% weight by volume was effective in killing a range of microorganisms both in the planktonic and biofilm state. Microorganisms that were effectively killed by EDTA included *Pseudomonas aeruginosa*, *Serratia marcescens*, vancomycin resistant *Enterococcus* (VRE) and methicillin resistant *Staphylococcus aureus* (M RSA).

EDTA is preferably present in the compositions of either aspect of the present invention at a level of 0.5% to 10% by weight of the composition, more preferably 1% to 3% by weight.

The compositions of the present invention may be in the form of a water based gel which maintains a moist wound healing environment and promotes healing. A gel gives the advantage of flow into the wound to form an intimate contact with the wound bed and provide antimicrobial effects to the whole wound. Preferably, the gel has a high enough viscosity that it does not flow out of wounds on areas of the body that are or become non-horizontal. Preferably, the pH of the gel is buffered at around 5.5 as this does not alter the pH balance of the peri-wound tissue and, therefore, protects it.

The following examples are illustrative of the present invention.

EXAMPLE 1

Effect of EDTA on Iodine

Compositions containing iodine and EDTA were prepared by making a pair of aqueous gels (see Table 1 for Gel A and Table 2 for Gel B) which were intimately mixed at the point of use. Each gel was made by preparing an aqueous solution containing all of the appropriate water-soluble parts according to the formulations below and then adding a slurry of a non-ionic cellulosic viscosifier (hydroxyethylcellulose) in propylene glycol.

TABLE 1

| Component | % w/w |
| --- | --- |
| Water | To 100 |
| Propan-1,2-diol | 10 |
| Hydroxyethylcellulose | 3.86 |
| Sodium iodate | 0.16 |
| Citric acid | 3.99 |
| di-sodium phosphate | 15.06 |

TABLE 2

| Component | % w/w |
| --- | --- |
| Water | To 100 |
| Propan-1,2-diol | 10 |
| Hydroxyethylcellulose | 4.14 |
| Sodium iodide | 0.59 |
| Ethylenediaminetetraacetic acid tetra-sodium salt tetrahydrate | 0.1-4.0 |
| Phosphoric acid | As necessary to adjust aqueous phase to ph 5.5 |

A commercially available cadexomer iodine ointment was present as a positive control as it contains 0.9% iodine. Intrasite is an amorphous hydrogel and was present as a negative control as it contains 0% iodine.

9 ml of simulated wound fluid was added to a 17 ml volume cell well. A 1 ml culture of *Staphylococcus aureus* was added to each well to give a final culture concentration of 106 cfu/ml. Controls for this experiment involved adding 2 g of cadexomor iodine ointment (positive control) and nydrogel (negative control) separately to three cell wells each. 1 g of gels A and B, with different concentrations of EDTA, were then added to separate cell wells (in triplicate). The cell wells containing the culture and gels were then shaken at 600 rpm at 35° C. After time intervals of 4, 24, 48, 72 and 96 hours, a 0.1 ml test sample was taken from each well and placed into 9.9 ml MRD (maximum recovery diluent) containing 1% sodium thiosulphate. A 1 ml sample was then transferred to Tryptone Soy Agar plates and incubated for 48 hours. Bacterial counts were then recorded.

TABLE 3

| Test composition | 4 hours | 24 hours | 48 hours | 72 hours | 96 hours |
| --- | --- | --- | --- | --- | --- |
| Iodosorb(positive control) | 10 | 10 | 10 | 10 | 10 |
| Intrasite(negative control) | 7600000 | 310000000 | 530000000 | 1000000000 | 14000000 |
| 0% I$_2$ 0% EDTA | 7600000 | 310000000 | 530000000 | 1000000000 | 14000000 |
| 0.3%/0I$_2$ 0% EDTA | 1240000 | 1000000 | 1000000 | 10000000 | 100000000 |
| 0.3%/0I$_2$ 0% EDTA | 1010000 | 1000000 | 1000000 | 10000000 | 100000000 |
| 0.3%/0I$_2$ 0% EDTA | 1670000 | 1000000 | 1000000 | 10000000 | 100000000 |

TABLE 3-continued

| Test composition | 4 hours | 24 hours | 48 hours | 72 hours | 96 hours |
|---|---|---|---|---|---|
| 0.3% $I_2$ 0.5% EDTA | 1500000 | 1000000 | 1000000 | 1000000 | 1000000 |
| 0.3% $I_2$ 0.5% EDTA | 92000 | 10 | 10 | 10 | 10 |
| 0.3% $I_2$ 0.5% EDTA | 58000 | 10 | 10 | 10 | 10 |
| 0.3% $I_2$ 1% EDTA | 8100 | 10 | 10 | 10 | 10 |
| 0.3% $I_2$ 1% EDTA | 130000 | 10 | 10 | 10 | 10 |
| 0.3% $I_2$ 1% EDTA | 110000 | 10 | 10 | 10 | 10 |
| 0.3% $I_2$ 1.75% EDTA | 710 | 10 | 10 | 10 | 10 |
| 0.3% $I_2$ 1.75% EDTA | 4400 | 10 | 10 | 10 | 10 |
| 0.3% $I_2$ 1.75% EDTA | 31000 | 10 | 10 | 10 | 10 |
| 0.3% $I_2$ 2.5% EDTA | 8500 | 10 | 10 | 10 | 10 |
| 0.3% $I_2$ 2.5% EDTA | 10600 | 10 | 10 | 10 | 10 |
| 0.3% $I_2$ 2.5% EDTA | 6200 | 16000 | 10 | 10 | 10 |
| 0.3% $I_2$ 4% EDTA | 93000 | 10 | 10 | 10 | 10 |
| 0.3% $I_2$ 4% EDTA | 8500 | 10 | 10 | 10 | 10 |
| 0.3% $I_2$ 4% EDTA |  | 1400 | 10 | 10 | 10 |

The results shown in Table 3 are also shown graphically in FIG. 1.

These results show that by adding as little as 0.5% EDTA (calculated as the di-sodium salt) to iodine, the efficacy of iodine, at 0.3%, is enhanced when compared to the control of 0.3% iodine with no EDTA. Clearly, from the results, EDTA enhances the effects of iodine within 24 hours to the same efficacy of 0.9% iodine (positive control).

EXAMPLE 2

Zones of Inhibition with Tetra Sodium EDTA

Seven antibiotic resistant microorganisms were used to evaluate the efficacy of EDTA in killing bacteria and yeasts grown on agar. For this experiment, filter paper discs were soaked in EDTA at concentrations ranging from 0.1-40%. EDTA was made up by dissolving it in an appropriate amount of sterile double distilled water. The filters were then added onto Muller Hinton agar which had been inoculated with a microorganism under study for 24 hours at 35° C. All microorganisms were tested twice.

Figure 2:
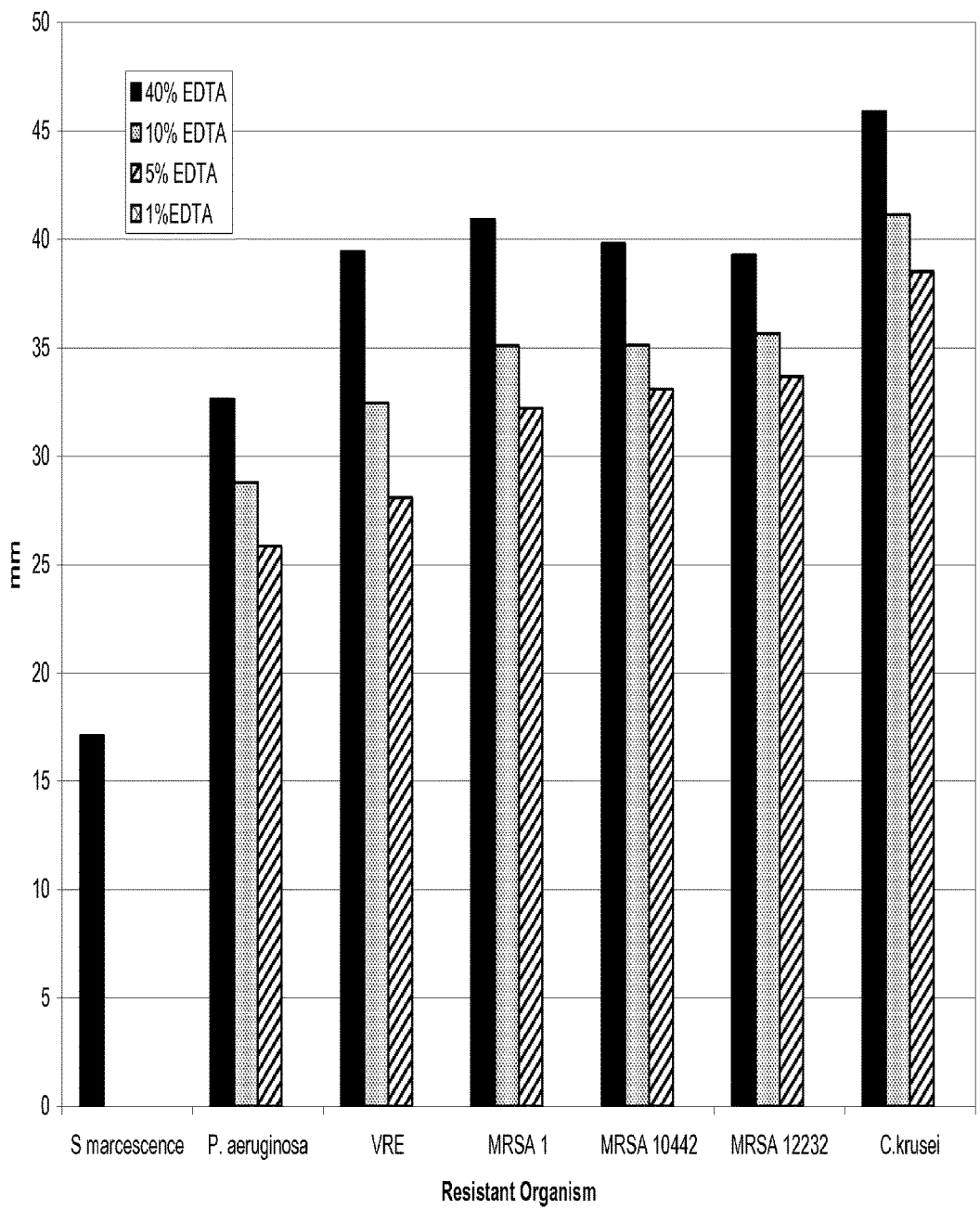
FIG. 2 is a graph showing zone of inhibition with EDTA.

The results in FIG. 2 show that the "zones of inhibition" generally ranged from about 20 to 43 mm (including disc 13 mm). Zones were higher with increasing levels of EDTA indicating that EDTA alone is an effective antiseptic agent.

EXAMPLE 3

Zones of Inhibition with EDTA

Poloxamer F127 hydrogels (Univar, Basildon, Essex, UK) are di-block co-polymers of polyoxyethylene and polyoxypropylene that demonstrate thermo-reversible gelation properties. At temperatures below 15° C., poloxamer is liquid and fully miscible with water but changes to a firm gel at temperatures in excess of 15° C. Poloxamer encourages bacteria to exhibit a more clinically relevant biofilm phenotype. In The Use of Poloxamer Hydrogels for the Assessment of Biofilm Susceptibility Towards Biocide Treatments. Gilbert P., Jones, M. V., Allison, D. G., Heys, S., Maira, T., Wood, P. Journal of Applied Microbiology (1998; 85:985-990), Gilbert, et al., determined that P. aeruginosa cells grown on poloxamer hydrogel (biofilm form) express outer membrane proteins between 78 and 87 kDa, which are not evident in cells grown on standard nutrient agar ('planktonic'). Consequently, poloxamer gel cultures mimic many of the properties of biofilm-grown P. aeruginosa (Gilbert et al., 1998). This indicates that there is a phenotypic difference between P. aeruginosa cells grown on poloxamer hydrogel and nutrient agar, with only poloxamer grown cells resembling biofilm cells. It was found from Wirtanen's study (Performance Evaluation of Disinfectant Formulations Using Poloxamer-hydrogel Biofilm-Constructs. Wirtanen, G., Salo, S., Allison, D. G., Mattila-Sandholm, T., Gilbert, P. Journal of Applied Microbiology (1998; 85:965-971)) that bacteria which are grown in poloxamer have biofilm properties and associated enhanced biocide resistance. Gilbert and colleagues suggested that bacteria grown in poloxamer hydrogels could be exposed to biocides to provide a reproducible method for testing the antimicrobial efficacy of biocides against biofilm bacteria (Gilbert, et al., 1998).

Seven antibiotic resistant microorganisms were used to evaluate the efficacy of EDTA in killing bacteria and yeasts grown on poloxamer gel (biofilm state). For this experiment, filter paper discs were soaked in EDTA at concentrations ranging from 0.1-40%. In this present study, poloxamer F127, a di-block copolymer of polyoxyethylene and polyoxypropylene, was used as a medium on which bacteria could be grown as a biofilm phenotype and express the characteristics more appropriate to the 'real world'. The filters were then added onto Muller Hinton agar which had been inoculated with the microorganism under study for 24 hours at 35° C. All plates were done in duplicate.

Figure 3:
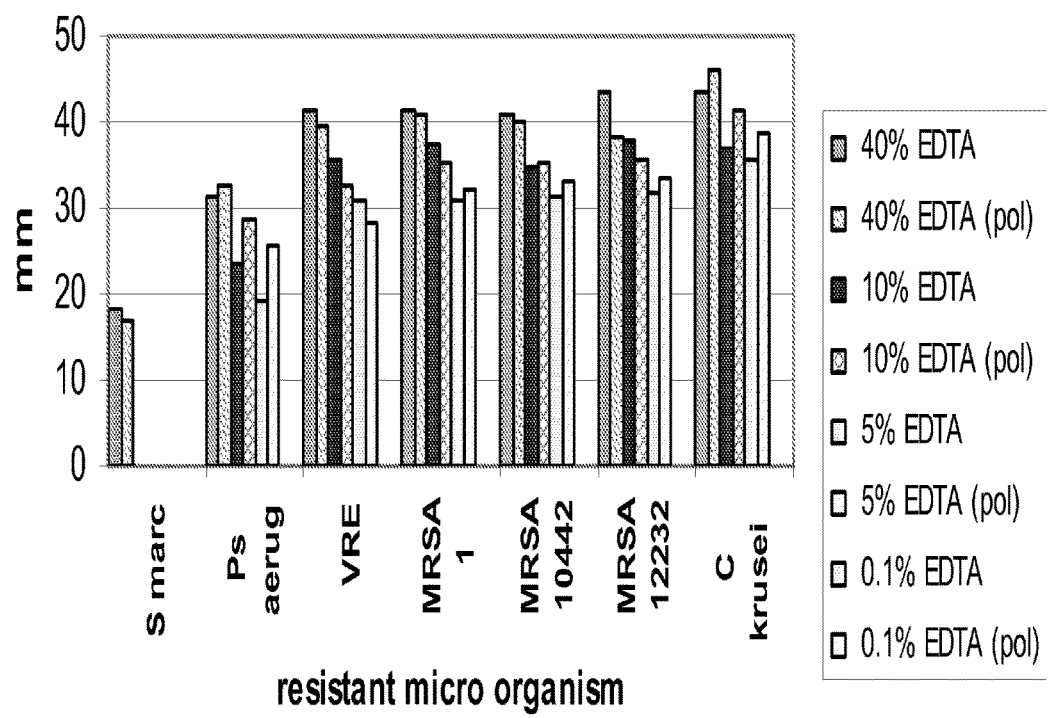
FIG. 3 is a graph showing zones of inhibition with EDTA, with and without poloaxmer.

The results in FIG. 3 show that the zones of inhibition were slightly smaller in the presence of poloxamer indicating that bacteria/yeasts growing as biofilms are physically more resistant to EDTA when compared to their planktonic couterparts. C. kruzei and P. aeruginosa were the exception with larger zones with poloxamer. Zones of inhibition were evident on all organisms tested at 40% EDTA. At 10% EDTA and 5% EDTA there were no zones with Serratia

*marcescens*. At 0.1% EDTA no zones of inhibition were evident with any organism studied indicating that EDTA is not effective at this level.

EXAMPLE 4

Minimum Inhibitory Concentrations (MIC's) and Minimum Bactericidal Concentrations (MBC's) with Tetra, Tri and Di Basic Salts of EDTA A microtitre plate and optical density readings and visual inspection were performed to obtain the MIC's for a variety of microorganisms (see Table 4). Concentrations of EDTA included in this study were 40 mg/ml pH 10.00 as tetra-Na, 40 mg/ml as tri-Na pH 6.84, 40 mg/ml as di-Na pH 5.50. Into each microtitre plate, 100 pl of inoculum and EDTA was added. The plate was then incubated for 24 hours at 35° C.±3° C. Following incubation all microtitre plates were inspected visually for growth.

The results are presented in Table 4.

TABLE 4

| MICRO ORGANISM | IDENTIFICATION | INOCULUM cfu | PvillC, s di Na | tri Na | tetra Na |
|---|---|---|---|---|---|
| S marcescens | multi res | 5.00E+04 | 0.938 | 1.875 | 0.938 |
| Ps aeruginosa | NCTC 8506 (res) | 6.75E+04 | 0.234 | 0.234 | 0.234 |
| Ps aeruginosa | NCIMB 8626 | 7.00E+04 | 0.938 | 0.938 | 0.938 |
| E coli | NCIMB 8545 | 5.50E+04 | 0.469 | 0.469 | 0.469 |
| E coli | NCIMB 10544 | <5.0+04 | 0.469 | 0.938 | 0.469 |
| KI pneumoniae | 033 clinical isolate | <5.0+E4 | 0.938 | 0.938 | 1.875 |
| Ent cloacae | 166 clinical isolate | 5.00E+04 | 1.875 | 0.938 | 0.938 |
| Pr mirabilis | NCTC 9559 | 1.50E+05 | 0.469 | 0.469 | 0.469 |
| A baumannii | NCIMB 9214 | 4.40E+04 | 0.234 | 0.234 | 0.469 |
| S aureus | NCIMB 9518 | 4.00E+04 | 0.234 | 0.234 | 0.234 |
| MRSA | 1 Cardiff PHL | 5.50E+04 | 0.117 | 0.469 | 0.234 |
| MRSA | 2 Cardiff PHL | 5.75E+04 | 0.234 | 0.469 | 0.234 |
| MRSA | 26 | 1.25E+04 | 0.234 | 0.234 | 0.234 |
| MRSA | NCTC 12232 | 5.00E+04 | 0.234 | 0.234 | 0.469 |
| MRSA | NCTC 10442 | 6.50E+04 | 0.234 | 0.234 | 0.234 |
| MRSA | 103731 Chester PHL | 6.00E+04 | 0.234 | 0.117 | 0.234 |
| Ent faecalis | 141 clinical isolate | 2.50E+04 | 0.234 | 0.234 | 0.234 |
| VRE | 1 Cardiff PHL | 2.75E+04 | 0.234 | 0.469 | 0.234 |
| VRE | 2 Cardiff PHL | 3.25E+04 | 0.234 | 0.234 | 0.234 |
| VRE | NCTC 12201 | 6.00E+04 | 0.234 | 0.234 | 0.234 |
| Strep pyogenes | NCTC 8198 | 7.00E+04 | 0.234 | 0.469 | 0.469 |
| B subtilis | NCTC 3610 | 3.00E+04 | 0.234 | 0.234 | 0.234 |
| C krusei | NCPF 3876 (res) | 1.50E+04 | 0.938 | 0.938 | 0.938 |
| B fragilis | NCIMB 9343 | 1.90E+05 | 0.117 | 0.234 | 0.234 |
| C/perfringens | 362 clinical isolate | 9.00E+03 | 0.117 | <0.117 | <0.117 |
| Pep anaerobius | NCTC 11460 | 1.30E+06 | 0.234 | 0.469 | 0.469 |

In general all MIC's recorded were equivalent for all the salts of EDTA studied. This suggests that the pH of the solutions is equivalent. Therefore, the activity of EDTA is not affected by the salt form added to the microtitre plate. These results show that low concentrations of EDTA are very effective on bacteria.

EXAMPLE 5

The Effect of EDTA on the Antimicrobial Efficacy of Silver Containing Wound Dressings The antimicrobial dressings used in this study were Acticoat™ (Smith and Nephew) and AQUACEL Ag Hydrofiber (ConvaTec). Acticoat™ is a nanocrystalline silver antimicrobial barrier dressing which consists of a rayon/polyester non-woven inner core laminated between two layers of silver-coated high density polyethylene mesh (HDPE). The layers are held together with ultrasound welds. AQUACELAg is comprised of sodium carboxymethylcellulose Hydrofiber and ionic silver. The silver cations in AQUACELAg are associated with the individual highly absorbent anionic carboxymethylcellulose fibres of the Hydrofiber dressing. AQUACELHydrofiber dressing (without silver) was also used as a control.

All dressings (AQUACELHydrofiber dressing [control—without silver], AQUACELAg and Acticoat™ (nanocrystalline dressing) were hydrated with 20 mg/ml of tetra-Na EDTA. All tests were performed against Ps acruginosa and tested on Mueller Hinton agar (MHA) and Poloxamer gel (incorporating Mueller Hinton broth (MHB). This involved inoculating either a MH agar plate or poloxamer gel plate with a specific isolate and then adding an appropriate hydrated (to saturation point) wound dressing (360 I (MRD) for AQUACEL and AQUACELAg and 150 I (sterile distilled water—as per manufacturers instructions) for Acticoat™). The plates were then incubated at 35° C.±3° C. for 24 hours after which the zone of clearance (no growth) around the dressing was measured. Zones of inhibition were measured horizontally and vertically (inclusive of the dressing sample) and a mean value was calculated from the duplicate set of results. The mean dressing size was then subtracted from the mean zone of inhibition to determine the corrected zone of inhibition (CZOI). A CZOI test allows for any inherent variability in the shape and size of zones created by the silver dressings which may change in dimension following hydration.

Table 5 shows the size of corrected zone of inhibition (CZOI) in mm on MH agar and poloxamer gel.

TABLE 5

| Hydrating Fluid | MHA (Non-biofilm bacteria) | | | Poloxamer gel with MHB (biofilm bacteria) | | |
|---|---|---|---|---|---|---|
| | AQUACEL | AQUACEL Ag | Acticoat | AQUACEL | AQUACEL Ag | Acticoat |
| EDTA | 0 | 16 | 10 | 6 | 6 | 7 |
| MRD | 0 | 18 | N/A | 0 | 3 | N/A |
| Water | N/A | N/A | 7 | N/A | N/A | 3 |

When EDTA was added to AQUACEL®, no zones of inhibition were observed on MHA (non-biofilm state). However, ZOI's were observed around AQUACELAg on MHA (non-biofilm bacteria) when EDTA or (maximal recovery diluent) MRD was added indicating the antimicrobial activity of silver. Larger ZOI's were observed around Acticoat™ following the addition of EDTA when compared to hydration with water. In the presence of poloxamer gel an increase in the CZOI was observed following hydration of AQUACELAg with MRD when compared to EDTA indicating an additive effect with the use of EDTA. Overall the results showed that EDTA enhances the effects of ionic silver on bacteria grown in the biofilm state (poloxamer gel). Overall these results suggest that by using an EDTA dressing it is effective against both planktonic and biofilm microorganisms.

Table 6 shows the size of corrected zone of inhibition in mm on MH agar and poloxamer gel.

TABLE 6

| Hydrating fluid | MHA (non-biofilm bacteria) | | | Poloxamer gel with MHB(biofilm bacteria) | | |
|---|---|---|---|---|---|---|
| | AQUACEL | AQUACEL Ag | Nano-crystalline silver dressing | AQUACEL | AQUACEL Ag | Nano-crystalline silver dressing |
| EDTA | 0 | 15.99 | 9.57 | 6.28 | 5.96 | 6.73 |
| MRD | 0 | 18.04 | N/A | 0 | 3.42 | N/A |
| Water | N/A | N/A | 6.74 | N/A | N/A | 2.82 |

EXAMPLE 6

Minimum Inhibitory Concentrations (MIC) for a Two Component Gel Comprising Iodine and a Two Component Gel as Detailed in Example 1 Containing EDTA (diNa EDTA, triNa EDTA and tetraNa EDTA)

This experiment shows the effect of pH on the activity of a range of EDTA forms.

For this experiment a two component gel as detailed in Example 1 was made without the HEC component (gel). This experiment was therefore performed using only liquid compositions (see Table 7 for TCG Solution (A) and Table 8 for TCG Solution (B)) in order for MIC's to be calculated. The pH of the TCG/EDTA solutions was approx 5.5. The organisms tested included: *Staphylococcus aureus, Pseudomonas aeruginosa, Escherichia coli* (repeated twice) and *C. albicans*.

TABLE 7

| Component | % w/w |
|---|---|
| Water | To 100 |
| Sodium iodate | 0.1 |
| Citric acid | 3.99 |
| di-sodium phosphate | 15.06 |

TABLE 8

| Component | % w/w |
|---|---|
| Water | To 100 |
| Sodium iodide | 0.4 |
| Ethylenediaminetetraacetic acid tetra-sodium salt tetrahydrate | As shown in Table 1 |
| Phosphoric acid | As necessary to adjust aqueous phase to pH 5.5 |

Table 9 shows MIC's for TCG solution and TCG solution combined with EDTA (values in brackets are EDTA concentrations in mg/ml)

TABLE 9

| Bacterium | TCG solution* | TCG EDTA | TCG and tri Na EDTA | TCG and tetra Na EDTA |
|---|---|---|---|---|
| S aureus | 0.25 (0) | 0.008 (0.31) | 0.008 (0.31) | 0.008 (0.31) |
| Ps aeruginosa | 0.5 (0) | 0.062 (2.5) | 0.062 (2.5) | 0.062 (2.5) |
| E coli | 0.25 (0) | 0.031 (1.25) | 0.031 (1.25) | 0.031 (1.25) |

*(working concentration was 0.2% iodine)

MIC's were reduced considerably in the presence of EDTA (di, tri and tetra Na). It can be seen that the MICs, expressed as Iodine concentration, are lower in the presence of di, tri and tetra sodium EDTA.

The antimicrobial benefit of having EDTA present is achieved at concentrations of 0.31 mg/ml. Despite different forms of EDTA being known to provide differential antimicrobial efficacy, at a constant pH (5.5 in this case) all EDTA forms were equally effective in significantly reducing the MIC's for all three organisms compared to the iodine generating solution without EDTA.

What is claimed is:

1. An antiseptic composition suitable for use on skin and wounds comprising 0.1% to 10% silver, EDTA, and buffering agent; wherein the pH is maintained between 4 and 6.

2. The antiseptic composition as claimed in claim 1, wherein the EDTA is present in the composition at a level of 0.1% to 10% by weight.

3. The antiseptic composition as claimed in claim 1, wherein the EDTA is in the form of the di-, tri- or tetra-basic salts of EDTA.

4. The antiseptic composition as claimed in claim 1, wherein the composition has a pH of between about 4.5 and 5.5.

5. The antiseptic composition as claimed in claim 1, wherein the composition is in the form of a gel.

6. The antiseptic composition as claimed in claim 1, wherein the antimicrobial agent is ionic silver.

7. The antiseptic composition as claimed in claim 6, wherein the composition comprises from about 0.5% to about 1.5% by weight of ionic silver.

* * * * *